United States Patent [19]

Stern et al.

[11] Patent Number: 5,728,480
[45] Date of Patent: Mar. 17, 1998

[54] POLY(4,5,9,10-TETRAHYDROPYRENE-2,7-DIYL) DERIVATIVES AND THEIR USE AS ELECTROLUMINESCENCE MATERIALS

[75] Inventors: Roland Stern, Wiesbaden; Donald Lupo, Frankfurt; Josef Salbeck, Kelkheim; Hermann Schenk, Hofheim; Thomas Stehlin, Kriftel; Klaus Müllen, Mainz; Martin Kreyenschmidt, Mainz; Ullrich Scherf, Mainz, all of Germany

[73] Assignee: Hoechst Aktiengesellschaft, Frankfurt, Germany

[21] Appl. No.: 521,263

[22] Filed: Aug. 30, 1995

[30] Foreign Application Priority Data

Sep. 1, 1994 [DE] Germany .................. 44 31 039.0

[51] Int. Cl.⁶ .............. H05B 33/12; C09K 11/06
[52] U.S. Cl. .............. 428/690; 428/411.1; 428/457; 428/917; 313/504; 313/506; 252/301.16; 252/301.35; 526/90; 526/171; 526/28; 526/281; 526/296; 528/397
[58] Field of Search .............. 428/411.1, 457, 428/690, 917; 313/504, 506; 252/301.35, 301.16; 526/90, 171, 280, 281, 296; 528/397

[56] References Cited

FOREIGN PATENT DOCUMENTS 0443861  8/1991  European Pat. Off. .
WO90/13148  11/1990  WIPO .

OTHER PUBLICATIONS

M. Kreyenschmidt et al., "A New Soluble Poly(p-phenylene) with Tetrahydropyrene Repeating Units", *Macromolecules*, vol. 28, No. 13, Jun. 19, 1995, pp. 4577–4582.
Chemical Abstracts, vol. 122, Jan. 1995, Columbus, Ohio, by M. Kreyenschmidt, et al., entitled "A new Soluble Poly(p-pheny-lens) with Tetrahydropyrene Repeating Units", p. 11.
Synthetic Metals by Grem et al., entitled "Blue Electroluminescent Device Based on a Conjugated Polymer", pp. 383–389, 1992.

J. Chem. Soc., Chem Communications by Ballard et al., entitled "A Bioteh Route to Polyphenylene", pp. 954–955, 1983.
PMSE–Meeting Chicago (1993), vol. 69, by Klavetter et al., entitled "Photoluminescence andElectroluminescence of Transparent Polyphenylene Derivatives", pp. 153–154.
Journal of Polymer Science, Part A. Polymer Chemistry, vol. 31, by Fukada et al., "Synthesis of Fusible and Soluble Conducting Polyfluorene Derivatives and their Characteristics", pp. 2465–2471, 1993.
Japanese Journal of Applied Physics, vol. 30, No. 11B,Nov. 191, by Ohmori et al., entitled "Blue Electroluminescent Diodes Utilizing Poly(alkylfluorene)", pp.1941–1943.

*Primary Examiner*—Marie Yamnitzky
*Attorney, Agent, or Firm*—Frommer Lawrence Haug LLP

[57] ABSTRACT

Poly(4,5,9,10-tetrahydropyrene-2,7-diyl) derivatives of the formula (I)

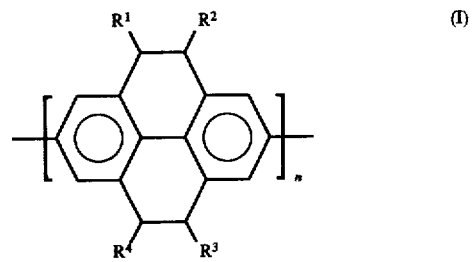

where the symbols $R^1$ to $R^4$ have the following meanings:

$R^1, R^2, R^3, R^4$ are identically or variously H, a straight-chain or branched alkyl chain containing 1 to 22 carbon atoms, it being possible for one or more nonadjacent $CH_2$ groups also to be replaced by —O—, —COO—, —OOC— and/or phenylene, aryl or aryloxy groups, it being possible for the aromatic to be substituted by $C_1$–$C_{22}$-alkyl, $C_1$–$C_{22}$-alkoxy, Br, Cl, F, CN, and/or $NO_2$, Br, Cl, F, CN, $NO_2$, or carboalkoxy containing 2 to 23 carbon atoms;

n is 10 to 150, are suitable as electroluminescence materials.

8 Claims, No Drawings

POLY(4,5,9,10-TETRAHYDROPYRENE-2,7-DIYL) DERIVATIVES AND THEIR USE AS ELECTROLUMINESCENCE MATERIALS

There is a high industrial requirement for large-area solid-state light sources for a number of applications, predominantly in the field of indicating elements, viewing screen technology and lighting engineering. The requirements imposed on said light sources cannot at present be achieved completely satisfactorily by any of the existing technologies.

As an alternative to conventional indicating and lighting elements, such as incandescent lamps, gas discharge lamps and non-self-luminous liquid crystal indicating elements, electroluminescence (EL) materials and devices, such as light-emitting diodes (LEDs), have already been in use for some time.

In addition to inorganic electroluminescence materials and devices, low-molecular-weight organic electroluminescence materials and devices have been known for about 30 years (see, for example, U.S. Pat. No. 3,172,862). Until recently, however, such devices were severely limited in their practical usability.

WO 90/13148 and EP-A 0 443 861 describe electroluminescence devices which contain a film composed of a conjugated polymer as light-emitting layer (semiconductor layer). Such devices offer numerous advantages, such as the possibility of producing large-area flexible displays in a simple and inexpensive manner. In contrast to liquid-crystal displays, electroluminescence displays are luminous and therefore do not require any additional rear lighting source.

A typical device according to WO 90/13148 comprises a light-emitting layer in the form of a thin, dense polymer film (semiconductor layer) which contains at least one conjugated polymer. A first contact layer is in contact with a first surface, a second contact layer is in contact with a further surface of the semiconductor layer. The polymer film of the semiconductor layer has a sufficiently low concentration of extrinsic charge carriers, so that when an electric field is applied between the two contact layers, charge carriers are introduced into the semiconductor layer, one contact layer being positive with respect to the other, and the semiconductor layer emits radiation. The polymers used in such devices are conjugated. Conjugated polymer is understood as meaning a polymer which has a delocalized electron system along the main chain. The delocalized electron system imparts semiconductor properties to the polymer and provides it with the possibility of transporting positive and/or negative charge carriers with high mobility.

In WO 90/13148, poly(p-phenylenevinylene) is used as polymeric material for the light-emitting layer and it is proposed to replace the phenyl group in such a material by a heterocyclic or a condensed carbocyclic ring system. In addition, poly(p-phenylene), PPP, is also used as electroluminescent material (G. Grem, G. Leditzky, B. Ullrich, G. Leising, Synth. Met. 1992, 51, page 383). The main problem in the synthesis and processing of PPP is to be perceived in the fact that this substance exhibits insolubility and infusibility even at very low degrees of polymerization. It was possible (see, for example, D. G. H. Ballard et al., J. Chem. Soc. Chem. Comm. 1983, page 954) to synthesize higher-molecular-weight PPP and to process it at the stage of a prepolymer via so-called precursor routes. However, these materials exhibit incomplete aromatization and/or ortho-linkages and other structural defects. In order to increase the processability of PPP and to make possible the synthesis of material having a higher degree of polymerization, derivatives having alkyl or alkoxy side chains have already been disclosed (F. L. Klavetter, G. G. Gustafsson, A. J. Heeger, PMSE-Meeting Chicago 1993, vol. 69, 153), which have a higher solubility. In this case, the alkyl or alkoxy side chains result in a severe twisting of the phenyl units and consequently in a drastic decrease in the n-orbital overlap along the polymer chain. Attempts to avoid this effect are based on the polymerization of 9,10-dihydrophenanthrenes and fluorenes. In the case of the polymerization of 9-alkyl- or 9,9-dialkylfluorenes by oxidative coupling with $FeCl_3$, it was possible to obtain materials having comparatively high molecular weight (degrees of polymerization in the order of magnitude of 10 repetition units) and for them to be used as active layer in electroluminescence devices (M. Fukada, K. Sawada, K. Yoshino, J. Polym. Sci. Part A, Polymer Chemistry 1993, 31, page 2465; Y. Ohmori, M. Uchida, K. Muro, K. Yoshino, Jpn. J. Appl. Phys. 1991, 30, page L1941). It was observed, however, that in this case defect points arise by linkage in positions 3 and 6.

Although good results were achieved with these materials, the color purity, for example, is still unsatisfactory. Furthermore, with the polymers known hitherto it is hardly possible to generate a blue or white emission.

Since, in addition, the development of electroluminescence materials, in particular based on polymers, cannot be considered as in any way complete, the manufacturers of lighting and indicating devices are interested in a very wide variety of electroluminescence materials for such devices.

This is also important, inter alia, because it is only the interaction of the electroluminescence materials with the further components of the devices which permits conclusions to be drawn about the quality of the electroluminescence material as well.

The object of the present invention was therefore to provide novel electroluminescence materials which, when used in a lighting or indicating device, are suitable for improving the property profile of said devices.

Surprisingly, it has now been found that certain derivatives of poly(4,5,9,10-tetrahydropyrene-2,7-diyl) have, in addition to an improved solubility in organic solvents and improved film-forming properties, in particular also good electroluminescence and photoluminescence with a high color purity.

The invention therefore relates to compounds of the formula (I),

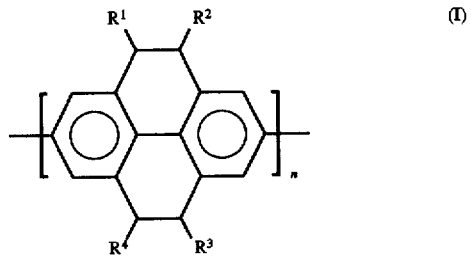

where the symbols $R^1$ to $R^4$ have the following meanings:
$R^1$, $R^2$, $R^3$, $R^4$ are identically or variously H, a straight-chain or branched alkyl chain containing 1 to 22 carbon atoms, it being possible for one or more nonadjacent $CH_2$ groups also to be replaced by —O—, —COO—, —OOC— and/or phenylene, aryl or aryloxy groups, preferably containing 4 to 10 carbon atoms, it being possible for the aromatic to be substituted with $C_1$–$C_{22}$-alkyl, $C_1$–$C_{22}$-alkoxy, Br, Cl, F, CN, and/or $NO_2$, Br, Cl, F, CN, $NO_2$, or carboalkoxy containing 2 to 23 carbon atoms;

n is 10 to 150.

Preferred are compounds of the formula (I) according to the invention in which $R^2$ and $R^4$ are hydrogen.

Preferred, furthermore, are compounds of the formula (I) in which $R^1$ is identical to $R^3$.

Particularly preferred are compounds according to the invention in which $R^2$ and $R^4$ are hydrogen and $R^1$ and $R^3$ are identical.

Preferred in particular are compounds of the formula (I) according to the invention in which $R^2$ and $R^4$ are hydrogen and in which $R^1$ and $R^3$ are identical and are a straight-chain or branched alkyl or alkoxy group containing 4 to 12 carbon atoms, an alkyl aryl group or a carboalkoxy group containing 5 to 13 carbon atoms.

The compounds of the formula (I) according to the invention are homopolymers or copolymers, i.e. the polymer of the formula (I) may also have different repetition units.

The compounds of the formula (I) according to the invention are well suited to achieving blue, yellow and white electroluminescence.

Advantages of the polymers according to the invention are, inter alia, the low tendency to crystallization and the good film-forming properties. The polymers according to the invention are furthermore distinguished by a considerable increase in the solubility in organic solvents. In addition, they are structurally uniform, not additionally sterically hindered despite the solubility-promoting side groups and have a comparatively high molecular weight.

The polymers according to the invention can be prepared by methods known per se in the literature, such as those described in the standard works on organic synthesis, for example Houben-Weyl, Methoden der Organischen Chemie, Georg-Thieme-Verlag, Stuttgart.

The preparation is carried out under reaction conditions which are known and suitable for the conversions mentioned. At the same time, use may also be made of variants which are known per se and are not mentioned in greater detail here.

Suitable as starting compounds for the preparation of the polymers according to the invention are, in general, two classes of monomers, on the one hand 4,5,9,10-tetrahydropyrenes which are optionally substituted in positions 4,5,9,10 and, on the other hand, 2,7-difunctionalized 4,5,9,10-tetrahydropyrenes which are optionally substituted in positions 4,5,9,10.

Methods known in the literature for the synthesis of the first class of monomers are based, for example, on transition-metal-catalyzed hydrogenations of pyrene [a) M. Minabe, K. Nakada, Bull. Chem. Soc. Jpn. 1985, 58, page 1962; b) P. P. Fu, H. M. Lee, R. G. Harvey, J. Org. Chem. 1980, 45, page 2797; c) R. G. Harvey, P. W. Rabideau, Tetrahedron Lett. 1979, page 3695]. Further synthesis paths for tetrahydropyrene are the cyclophane route [a) T. Sato, M. Wakabayashi, Y. Okamura, Bull. Chem. Soc. Jpn. 1967, 40, page 2365; b) T. Yamato, S. Ide, K. Tokuhisa, M. Toshiro, J. Org. Chem. 1992, 57, page 271] and the photochemical cyclization of distyrylbiphenyl [a) A. Padwa, A. Mazzu, Tetrahedron Lett. 1974, page 4471; b) P. H. G. op het Veld, J. C. Langendannn, W. H. Laarhoven, Tetrahedron Lett. 1975, page 231].

The literature also offers examples of the introduction of substituents into positions 4,9, such as the photocyclization of substituted distyrylbiphenyls. 4,5,9,10-Tetrahydropyrenes which are substituted symmetrically in positions 4 and 9 are prepared by this method. The substituents are substituted or unsubstituted aryls [a) P. H. G. op het Veld, J. C. Langendamm, W. H. Laarhoven, Tetrahedron Lett. 1975, page 231; b) W. H. Laarhoven, Th. J. H. M. Cuppen, J. C. S. Perkin 1 1972, page 2074; c) P. H. G. op het Veld, W. H. Laarhoven, J. C. S. Perkin 2 1977, page 268; d) P. H. G. op het Veld, W. H. Laarhoven, J. C. S. Perkin 2 1977, page 922; e) J. Meinwald, J. W. Yound, J. Am. Chem. Soc. 1971, 93, page 725], carboxylates and cyano groups [a) A. Padwa, C. Doubleday, A. Mazzu, J. Org. Chem. 1977, vol. 42, page 3271; b) A. Padwa, A. Mazzu, Tetrahedron Lett. 1974, page 4471]. Starting from pyrene, 4,5,9,10-tetrahydroxy-4,5,9,10-tetrahydropyrene [a) R. M. Moriarty, P. Dansette, D. M. Merina, Tetrahedron Lett. 1975, 30, page 2557] and 4,5,9,10-pyreneterones [a) E. Clar, H. Becker, M. Correl, H. Streeck, Ann. 1937, 531, page 1; b) J. K. Stille, E. L. Mainen, Macromolecules 1968, 1, page 36] and 4,5,9,10-pyrenebisoxirane are synthesized.

4,5,9,10-Tetrahydropyrenes having substituents in positions 4,9 are synthesized from the corresponding dialkylvinylbiphenyl derivatives by the abovementioned photocyclization. The method offers the prerequisite for introducing a great variety of substituents into positions 4 and 9, as the synthesized examples show. At the same time, the corresponding dialkylvinylbiphenyl derivatives can be prepared either from diphenaldehyde and a phosphonium salt or from 2,2'-bis(triphenylphosphoniomethyl)biphenyl dibromide and a suitable aldehyde by the known Wittig reactions. In order to introduce substituents into positions 5 and 10 as well, the starting point is not diphenaldehyde, but the corresponding diketone, which may also contain variable substituents and is reacted with methyltriphenylphosphonium bromide to form the dialkylvinylbiphenyl derivative which is then photocyclized to form 5,10-disubstituted tetrahydropyrene. It is furthermore possible to prepare a product which can be reacted to form a fourfold-substituted tetrahydropyrene by reacting the diketone cited with various phosphonium salts. At the same time, an asymmetry can be introduced into the molecule in this way by means of the various substituents.

A further path for synthesizing doubly substituted or fourfold-substituted 4,5,9,10-tetrahydropyrene derivatives proceeds via diols or tetraols by reacting the latter to form the respective ethers, esters or other functionalizations.

It is also possible to introduce substituents by brominating the corresponding tetrahydropyrene in the benzyl positions and introducing, for example, alkyl groups by reaction with alkyl Grignard compounds with nickel catalysis or by the reaction with the corresponding boronic acids in accordance with Suzuki or Miller (see below).

To prepare the second class of monomers, functions have to be introduced into position 2 and 7 of the tetrahydropyrene.

Two synthesis paths are preferred, which are shown by way of example in schemes 1 and 2.

Scheme 1

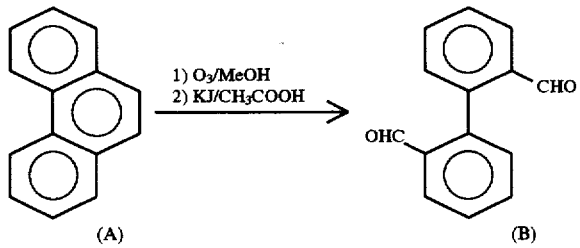

(A)  (B)

-continued
Scheme 1
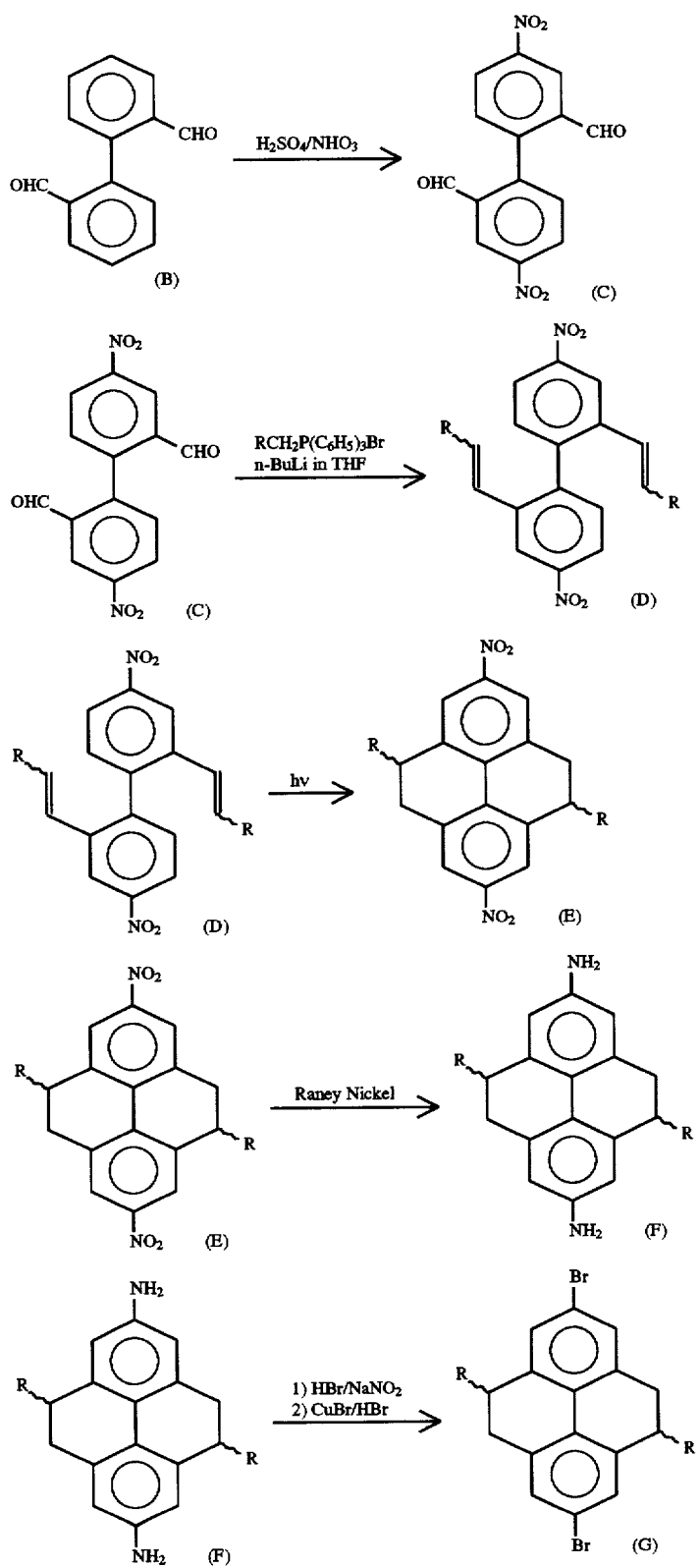

According to scheme 1, phenanthrene (A) is reacted by ozonolysis and subsequent oxidization of the ozonide with sodium iodide to form diphenaldehyde (B). The latter can be nitrated with $HNO_3/H_2SO_4$ to form the dinitro compound (C), which is then converted into the 4,4'-dinitro-2,2'-divinylbiphenyl derivative (D) by a Wittig reaction. (D) is cyclized photochemically to form the tetrahydropyrene derivative (E). This intermediate makes possible a variable functionalization in positions 2 and 7 since the nitro group can be replaced by a multiplicity of other functional groups. As an example, the synthesis of the dibromo compound (G) by reduction of the dinitro compound (E) to the diamine (F) and subsequent Sandmeyer reaction is shown in scheme 1.

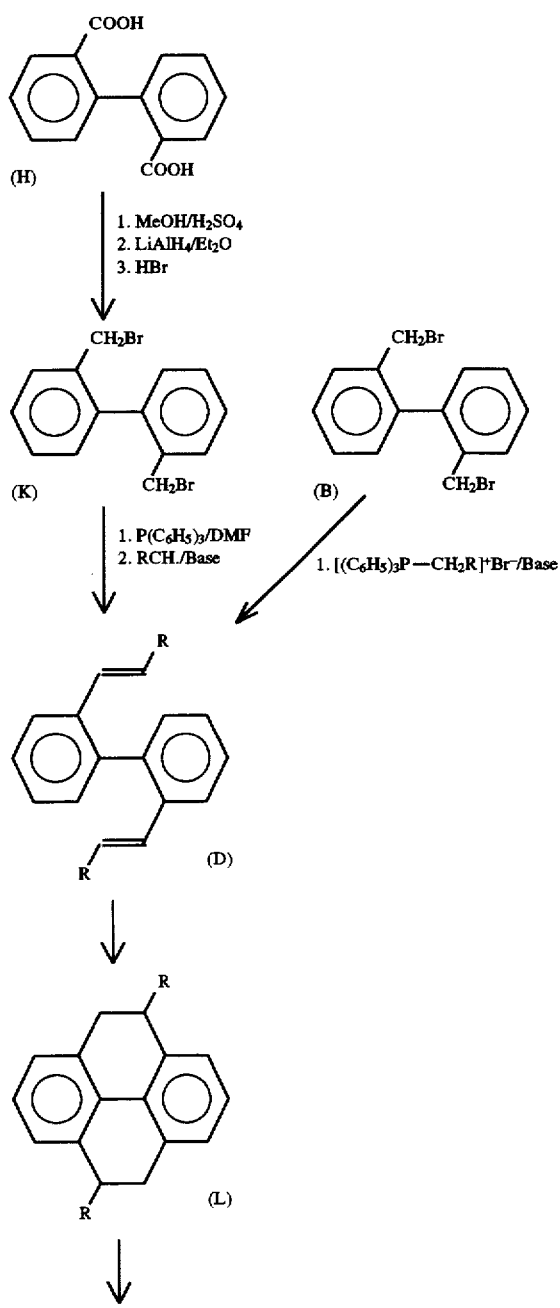

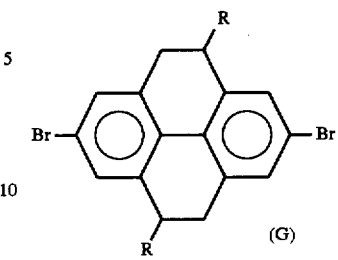

A second path to 2,7-difunctionalized 4,5,9,10-tetrahydropyrene derivatives is shown by way of example in scheme 2.

Diphenic acid (H) is reacted with methanol to form the dimethyl ester, which is reduced with lithium aluminum hydride to form the 2,2'-bishydroxymethylbiphenyl. Substitution of the hydroxy groups by bromine by means of HBr then leads to dibromo compound (K). A biphosphonium salt which, after deprotonation to phosphorane, reacts with aldehydes to form the divinyl compound (D) is prepared from (K) by reaction with triphenylphosphine. Alternatively, (B) can also be prepared from the diphenyl aldehyde (B) described in scheme 1 by Wittig reaction. The vinyl compound (D) is reacted by photocyclization to form the 4,5,9,10-tetrahydropyrene derivative (L).

From the latter, the dibromo compound (G) described above can be prepared by a novel bromination method, to which the invention also relates. The novel process for preparing 2,7-dibromo-4,5,9,10-tetrahydropyrene derivatives comprises reacting a 4,5,9,10-tetrahydropyrene derivative with bromine in an inert organic solvent in the presence of a metal of group 8 on active carbon as support material.

The process according to the invention is characterized, in particular, by its excellent selectivity; bromination takes place exclusively in positions 2 and 7.

The process is carried out, in general, at a temperature of $-50°$ to $100°$ C., preferably $0°$ to $50°$ C., particularly preferably at room temperature.

Preferred are strongly polar, protic or aprotic solvents, such as DMF and water.

In the process according to the invention, a metal of group 8 on activicarbon serves as catalyst.

Preferably, palladium, platinum, iridium or nickel, particularly preferably palladium or platinum, in particular palladium, is used as metal of group 8.

Preferred catalysts contain about 5 to 10% by weight of metal on the active carbon.

The catalyst is preferably used in an amount of 0.2 to 20 mol %, particularly preferably of 1 to 4 mol %, based on the tetrahydropyrene derivative.

Preferably, 0.9 to 3 equivalents of bromine are used per bromine function in the target molecule.

The working-up is carried out by known methods familiar to the person skilled in the art. For example, excess bromine is destroyed by adding aqueous NaOH or $NaHSO_3$ solution, diluting with water, extracting with a water-insoluble organic solvent and purifying the crude product, obtained after drying and distilling off the solvent, by chromatography.

The 2,7-dibromo-4,5,9,10-tetrahydropyrene derivatives prepared by this process are eminently suitable as starting products for the preparation of polymers of the formula (I) according to the invention.

They can be reacted equally as well by methods known in the literature, for example, to form diboronic acids (M. Miyaura, T. Yanagi, A. Suzuki, Synth. Commun. 1981, 11, 513; R. B. Miller, S. Dugar, Organometallics 1984, 3, 1261), mixed bromoboronic acids (M. Rehahn, A. D. Schlüter, G. Wegner, W. J. Feast, Polymer 1989, 30, 1054) or distannanes (J. K. Stille, Angew. Chem. Int. Ed. Engl. 1986, 25, 508), which are also starting compounds for the polymers according to the invention.

The preparation of the polymers of the formula (I) according to the invention is possible by a plurality of methods.

For example, derivatives of 4,5,9,10-tetrahydropyrene can be polymerized oxidatively (for example, with $FeCl_3$, see, inter alia, P. Kovacic, N. B. Jones, Chem. Ber. 1987, 87, 357 to 379; M. Weda, T. Abe, H. Awano, Macromolecules 1992, 25, 5125) or electrochemically (see, for example, N. Saito, T. Kanbara, T. Sato, T. Yamamoto, Polym. Bull. 1993, 30, 285).

The polymers of the formula (I) according to the invention can also be prepared from 2,7-difunctionalized 4,5,9, 10-tetrahydropyrene derivatives. Dihaloaromatics can be polymerized with copper/triphenylphosphine catalysis (see, for example, G. W. Ebert, R. D. Rieke, J. Org. Chem. 1988, 53, 44829) or with nickel/triphenylphosphine catalysis (see, for example, H. Matsumoto, S. Inaba, R. D. Rieke, J. Org. Chem. 1983, 48, 840).

Aromatic diboronic acids and aromatic dihalides or mixed aromatic haloboronic acids can be polymerized with palladium catalysis by coupling reactions (see, for example, M. Miyaura, T. Yanagi, A. Suzuki, Synth. Commun. 1981, 11, 513; R. B. Miller, S. Dugar, Organometallics 1984, 3, 1261).

Aromatic distannanes can be polymerized, for example, with palladium catalysis, as specified in J. K. Stille, Angew. Chem. Int. Ed. Engl. 1986, 25, 508.

Furthermore, the dibromo compounds mentioned above can be converted into the dilithio or di-grignard compounds which are then polymerized with further dibromo compounds by means of $CuCl_2$ (see, for example, G. Wittig, G. Klar, Liebigs Ann. Chem. 1967, 704, 91; H. A. Stabb, F. Bunny, Chem. Ber. 1967, 100, Kaufmann, Angew. Chem. 1974, 86, 321 to 354) or by electron transfer of unsaturated 1,4-dihalo compounds (see, for example, S. K. Taylor, S. G. Bennett, K. J. Harz, L. K. Lashley, J. Org. Chem. 1981, 46, 2190).

Preferred is a process for the preparation of polymers of the formula (I)

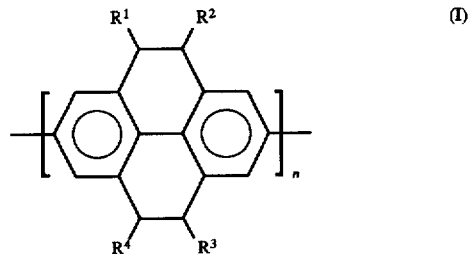

where the symbols $R^1$ to $R^4$ have the following meanings:

$R^1$, $R^2$, $R^3$, $R^4$ are identically or variously H, a straight-chain or branched alkyl chain containing 1 to 22 carbon atoms, it being possible for one or more nonadjacent $CH_2$ groups also to be replaced by —O—, —COO—, —OOC— and/or phenylene, aryl or aryloxy groups, it being possible for the aromatic to be substituted with $C_1$–$C_{22}$-alkyl, $C_1$–$C_{22}$-alkoxy, Br, Cl, F, CN, and/or $NO_2$, Br, Cl, F, CN, $NO_2$, or carboalkoxy containing 2 to 23 carbon atoms;

n is 10 to 150, which comprises reacting one or more compounds of the formula (II)

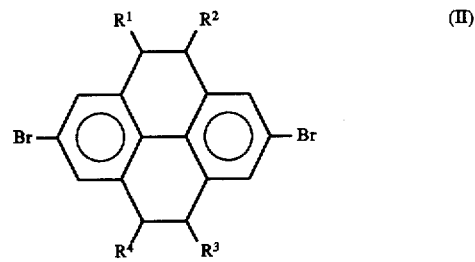

in which the symbols have the same meanings as in the formula (I), with bis(1,5-cyclooctadiene)nickel(0) and a 2,2'-bipyridine in an inert organic solvent or solvent mixture.

The reaction takes place in general at a temperature of 0° to 150° C., preferably 20° to 100° C., particularly preferably 40° to 90° C. The reaction time is in general 1 to 7, usually 2 to 3, days.

Preferred solvents are N,N-dialkylamides, such as dimethylformamide (DMF), ethers, such as tetrahydrofuran (THF), aromatic hydrocarbons, such as toluene and mixtures of the solvents cited.

Particularly preferred is a mixture of DMF and toluene, in particular in the ratio 1:3.

Bis(1,5-cyclooctadiene)nickel(0) ($Ni(COD)_2$) can be used directly, but it can also be formed in situ in the reaction mixture composed of 1,5-cyclooctadiene and a nickel complex, such as $Ni(dppp)Cl_2$, $Ni(acac)_2$, $Ni(bipy)Cl_2$ or $Ni(PPh_3)_2Cl_2$. Preferably, the reaction mixture always contains an excess of cyclooctadiene.

The 2,2'-bipyridine used may optionally be substituted; in general it is used in excess, based on the nickel complex. 0.9 to 2, preferably 1 to 1.5, particularly preferably 1.2 to 1.3, equivalents of the coupling reagent ($NiCoD_2$) ( 2,2 -dipyridine) are used per bromine atom.

To prepare copolymers, for example, various compounds of the formula (II) can be polymerized jointly.

The working up is carried out by known methods familiar to the person skilled in the art. For example, the reaction mixture can be filtered, diluted with aqueous acid and extracted, and the crude product obtained after drying and distilling of the solvent purified further by reprecipitation.

Terminal bromine atoms can be removed reductively, for example, with $LiAlH_4$.

The polymers according to the invention can be used as electroluminescence materials, i.e. they serve as active layer in an electroluminescence device. An active layer for the purpose of the invention is considered to be electroluminescence materials which are capable of radiating light when an electric field is applied (light-emitting layer) and materials which improve the injection and/or the transport of the positive and/or negative charges (charge-injection layers and charge-transport layers).

The invention therefore also relates to the use of polymers of the formula (I) according to the invention as electroluminescence materials and also to electroluminescence materials containing a polymer of the formula (I).

The invention furthermore relates to an electroluminescence device having one or more active layers, at least one of said active layers containing one or more polymers according to the invention. The active layer may, for example, be a light-emitting layer and/or a transport layer and/or a charge-injection layer.

The general structure of such electroluminescence devices is described, for example, in U.S. Pat. No. 4,539,507 and U.S. Pat. No. 5,151,629. Polymer-containing electroluminescence devices are described, for example, in WO 90/13148 or EP-A 0 443 861.

They usually contain an electroluminescent layer between a cathode and an anode, at least one of the electrodes being transparent. Additionally, an electron-injection and/or electron-transport layer can be introduced between the electroluminescent layer and the cathode and/or a hole-injection and/or hole-transport layer can be introduced between the electroluminescent layer and the anode. Ca, Mg, Al, In, Mg/Ag, for example, may serve as cathode. Au or ITO (indium oxide/tin oxide), for example, on a transparent substrate, for example composed of glass or a transparent polymer, may serve as anode.

During operation, the cathode is set at a negative potential with respect to the anode. Under these circumstances electrons are injected from the cathode into the electron-injection layer/electron-transport layer or directly into the light-emitting layer. Simultaneously, holes are injected from the anode into the hole-injection layer/hole-transport layer or directly into the light-emitting layer.

The injected charge carriers migrate toward one another through the active layers under the influence of the applied voltage. At the interface between charge-transport layer and light-emitting layer or inside the light-emitting layer, this results in electron/hole pairs which recombine with the emission of light.

The color of the emitted light can be varied by the compound used as light-emitting layer.

Electroluminescence devices are used, for example, as self-luminous indicating elements, as pilot lamps, as alphanumerical displays, as indicating boards and in optoelectronic couplers.

The invention is explained in greater detail by the examples without wishing to restrict it thereby.

EXAMPLES

Example 1

Cis-transisomers of 2,2'-dodecyl-1"-enebiphenyl

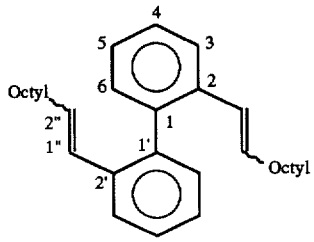

Empirical formula: $C_{32}H_{46}$
Molecular weight: 430.5 g/mol
Melting point: colorless oil

Description of Synthesis 84 g (0.1 mol) of 2,2'-bis(triphenylphosphoniomethyl) biphenyl dibromide and 42.6 g (0.3 mol) of nonanal are dissolved in 400 ml of absolute EtOH in a 1 l three-neck flask which has been rendered inert and which has a reflux condenser and a dropping funnel, and heated to 75° C. 500 ml of 0.5 molar sodium alcoholate solution are added dropwise in the course of 4 hours, a yellow coloration appearing as a result of the formation of the ylid. Stirring is continued for 20 hours at 75° C. and, after it has been cooled and 800 ml of $H_2O$ have been added, the solution is extracted three times with methylene chloride. The combined organic phases are dried over $MgSO_4$ and the solvent is distilled off in vacuo. The purification is carried out by column chromatography on silica gel with petroleum ether/ether (20:1). Yield: 36 g (87%).

Example 2

Cis-transisomers of 4,9-dioctyl-4,5,9,10-tetrahydropyrene

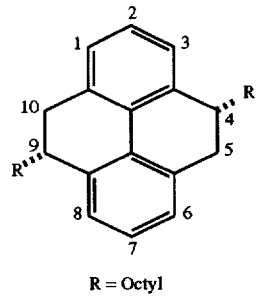

R = Octyl

Empirical formula: $C_{32}H_{46}$
Molecular weight: 430.5 g/mol
Melting point: colorless oil

Description of Synthesis 2.154 g (0.005 mol) of 2,2'-didecyl-1"-enebiphenyl are dissolved in 300 ml of n-hexane and poured into a photoreactor. A stream of argon is now passed through the solution for 30 minutes while stirring in order to remove the residual oxygen as far as possible. Then irradiation is carried out under a gentle stream of argon for between 5 and 6 hours at a wavelength of 254 nm (80 watts) using an Hg low-pressure immersion lamp supplied by the Gräntzel company. The end of the photoreaction is determined by $^1$H-NMR. The solvent is distilled off in a rotary evaporator, a yellowish oil remaining which is chromatographed on silica gel using petroleum ether/ether (20:1). Yield: 2.01 g (94%).

Example 3

Cis- or trans-2,7-dibromo-4,9-dioctyl-4,5,9,10-tetrahydropyrene

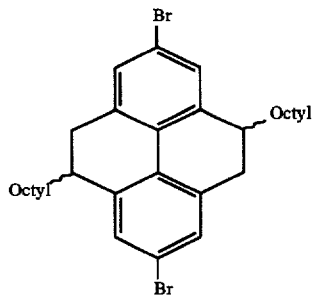

Empirical formula: $C_{32}H_{44}Br_2$
Molecular weight: 588.5 g/mol
Melting point: oil

Description of Synthesis 10.75 g (0.025 mol) of 4,9-dioctyl-4,5,9,10-tetrahydropyrene are dissolved in 170 ml of DMF in a 250 ml two-neck flask with a dropping funnel, 100 mg of 5%-strength palladium on active charcoal are added and 11.98 g (3.85 ml, 0.075 mol) of bromine in 40 ml of DMF are added dropwise in the course of 2 hours at room temperature while stirring and excluding light. The reaction is allowed to continue for 12 to 16 hours; then excess bromine is destroyed by adding a 15%-strength by weight NaOH solution. 200 ml of water are added and extraction is carried out three times with 50 ml of methylene chloride. To remove the palladium catalyst, filtering is carried out through Celite® (filtering aid supplied by the company Aldrich, Steinheim), then drying is carried out over magnesium sulfate and the solvent is distilled off. The yellow oil is chromatographed twice over aluminium oxide and twice over silica gel, using petroleum ether in each case. The first isomer (trans) accumulates in each case in the first fractions and 52% (7.65 g) is formed as a colorless oil which crystallizes out in white form after a few days.

33% of the second isomeric fraction can also be obtained as a colorless oil which also crystallizes out after a few days.

Example 4

Poly(4,9-dioctyl-4,5,9,10-tetrahydropyrene-2,7-diyl)

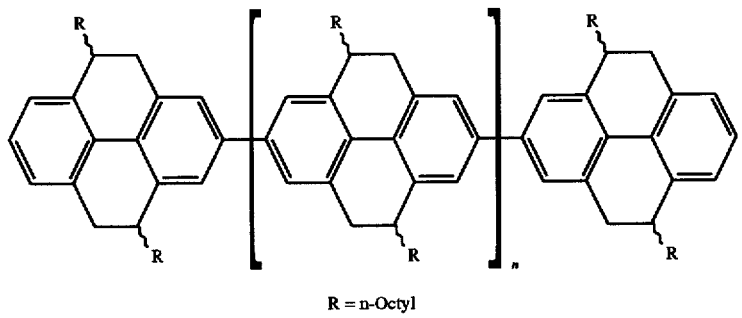

R = n-Octyl

Empirical formula: $C_{32x}H_{44x}$
Weight of the monomer unit: 428.704 g/mol
Melting point: 270° C. (TGA)

Description of Synthesis

A coupling reagent is prepared from 1.1 g (0.00377 mol) of Ni(COD)$_2$, 650 mg (0.00436 mol) of 2,2'-bipyridyl and 434 mg (0.35 ml) of cyclooctadiene in 7 ml of absolute DMF and 10 ml of absolute toluene in a 100 ml Schlenck tube which has been rendered inert and is flooded with argon. The solution is deep blue to purple in color and is stirred for 30 minutes at 70° C. In a separately de-gassed 50 ml Schlenck flask, 1.491 g (0.00254 mol) of 2,7-dibromo-4,9-dioctyl-4,5,9,10-tetrahydropyrene are dissolved in a 12 ml of absolute toluene, heated to 50° C. and added by injecting to the solution of the coupling reagent. The solution becomes red-brown colored after a few moments and stirring is carried out for 3 days at 75° C. with light excluded. The solution is cooled and filtered over Celite® (filtering aid supplied by the company Aldrich, Steinheim), and it is added to 100 ml of 5N aqueous HCl and is allowed to thoroughly mix for 1 hour on a magnetic stirrer. The aqueous solution is then extracted three times with 50 ml of CHCl$_3$ and the combined organic phases are washed three times with 150 ml of aqueous EDTA solution having a pH=9 and three times with 150 ml of aqueous EDTA solution having a pH=3.8, and also a further two times with 150 ml of 5N aqueous HCl and then repeatedly with water. The combined organic phases are dried over MgSO$_4$ and the solvent is evaporated off in vacuo. To remove terminal bromine atoms, a suspension of 5 g of LiAlH$_4$ in 50 ml of absolute THF is made up in a 250 ml three-neck flask with reflux condenser and septum which has been rendered inert and vented with argon and the polymer, dissolved in 50 ml of absolute toluene, is injected via the septum. Heating is then carried out for 3 days under reflux. After cooling in an ice-bath, the reaction mixture is hydrolyzed with 25 ml of 2N H$_2$SO$_4$ and 200 ml of H$_2$O are then added. The solution is extracted repeatedly with 100 ml of CHCl$_3$, the combined organic phases are dried over magnesium sulfate and the solvent is evaporated down to 10 ml in vacuo. The polymer is now precipitated in 100 ml of acetone and filtered through a frit by suction. The color of the polymer is light yellow.

Example 5

Electroluminescence Device

A solution of poly (4,9-dioctyl-4,5,9,10-tetrahydropyrene-2,7-diyl) in chloroform (15 mg/ml) is applied by spin coating at 1000 rev/min under nitrogen to a glass substrate coated with ITO (indium tin oxide) (structured, strips 2 mm wide). The glass substrate is transferred to a high-vacuum vapor-deposition system via a lock while retaining the protective gas atmosphere. Ca strips (2 mm wide, 230 nm thick) are vapor-deposited on the polymer layer at 2×10$^{-5}$ mbar perpendicular to the ITO strips using a mask. The device obtained in this way, ITO/Poly(4,9-dioctyl-4,5,9,10-tetrahydropyrene-2,7-diyl)/Ca, is introduced into a specimen holder and the electrodes are connected via spring contacts to a current source, an ITO strip being polarized positively and a Ca strip negatively. When a voltage of 23 V is applied, an intense, homogeneous blue fluorescence (11 cd/m$^2$ at 0.27 mA; under argon atmosphere) is observed at the corresponding matrix element. The external efficiency is 0.11%. The electroluminescence spectrum essentially corresponds to the photoluminescence spectrum photoluminescence of a film applied to a quartz substrate by means of spin coating).

We claim:

1. A poly (4,5,9,10-tetrahydropyrene-2,7-diyl) derivative of formula (I)

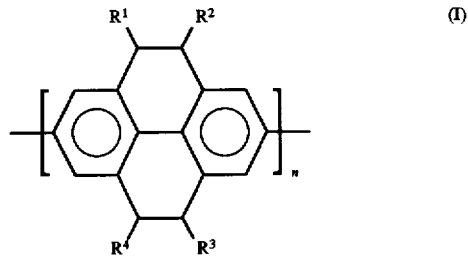

where the symbols R$^1$ to R$^4$ have the following meanings:
R$^1$, R$^2$, R$^3$, R$^4$ are identically or variously H, NO$_2$, Br, Cl, F, CN, a carboalkoxy containing 2 to 23 carbon atoms or a straightchain or branched alkyl chain containing 1 to 22 carbon atoms, it being possible for one or more nonadjacent CH$_2$ groups also to be replaced by —O—, —COO—, —OOC— or phenylene, aryl or aryloxy groups, it being possible for said phenylene, aryl or aryloxy groups to be substituted by one or more of $C_1$–$C_{22}$-alkyl, $C_1$–$C_{22}$-alkoxy, Br, Cl, F, CN and $NO_2$;

n is 10 to 150.

2. A poly(4,5,9,10-tetrahydropyrene-2,7-diyl) derivative as claimed in claim 1, which is a homopolymer.

3. A poly(4,5,9,10-tetrahydropyrene-2,7-diyl) derivative as claimed in claim 1, which is a copolymer.

4. A poly(4,5,9,10-tetrahydropyrene-2,7-diyl) derivative as claimed in claim 1, wherein $R^2$ and $R^4$ in the formula (I) are H.

5. A poly(4,5,9,10-tetrahydropyrene-2,7-diyl) derivative as claimed in claim 1, wherein, in the formula (I)

$R^2$ and $R^4$ are H and $R^1$ and $R^3$ are identically Br, Cl, F, CN, $NO_2$, a carboalkoxy containing 2 to 23 carbon atoms, or a straight-chain or branched alkyl chain containing 1 to 22 carbon atoms, it being possible for one or more nonadjacent $CH_2$ groups also to be replaced by —O—, —COO—, —OOC— or phenylene, aryl or aryloxy groups, it being possible for said phenylene, aryl or aryloxy groups to be substituted by one or more of $C_1$–$C_{22}$-alkyl, $C_1$–$C_{22}$-alkoxy, Br, Cl, F, CN and $NO_2$;

n is 10 to 150.

6. A process for preparing compounds of the formula (I) as claimed in claim 1, which comprises reacting one or more compounds of the formula (II)

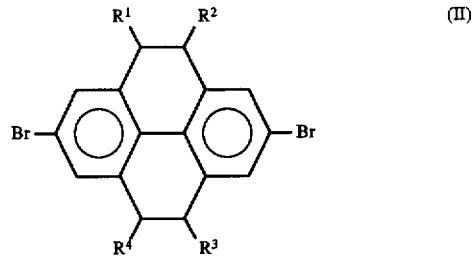

(II)

in which the symbols $R^1$ to $R^4$ have the same meanings as in formula (I), with bis(1,5-cyclooctadiene)nickel(0) and a 2,2'-bipyridine in an inert organic solvent or solvent mixture.

7. An electroluminescence material comprising one or more poly(4,5,9,10-tetrahydropyrene-2,7-diyl) derivatives as claimed in claim 1.

8. An electroluminescence device comprising an electroluminescent layer between a cathode and an anode, wherein said device comprises a poly(4,5,9,10-tetrahydropyrene-2,7-diyl) derivative as claimed in claim 1 as electroluminescence material.

* * * * *